(12) United States Patent
Merilainen

(10) Patent No.: US 6,961,603 B2
(45) Date of Patent: Nov. 1, 2005

(54) UNITARY MULTI-ELECTRODE BIOPOTENTIAL SIGNAL SENSOR AND METHOD FOR MAKING SAME

(75) Inventor: Pekka Merilainen, Helsinki (FI)

(73) Assignee: Instrumentarim Corp., Helsinki (FI)

( * ) Notice: Subject to any disclaimer, the term of this patent is extended or adjusted under 35 U.S.C. 154(b) by 193 days.

(21) Appl. No.: 10/463,500

(22) Filed: Jun. 17, 2003

(65) Prior Publication Data
US 2004/0260166 A1 Dec. 23, 2004

(51) Int. Cl.$^7$ ................................ A61B 5/04
(52) U.S. Cl. ...................... 600/383; 600/393
(58) Field of Search ................ 600/373, 382, 600/383, 393; 607/115, 116, 139, 148

(56) References Cited

U.S. PATENT DOCUMENTS

| | | | |
|---|---|---|---|
| 3,776,228 A | * 12/1973 | Semler | ............ 600/523 |
| 4,072,145 A | 2/1978 | Silva | |
| 4,082,087 A | 4/1978 | Howson | |
| 4,353,372 A | 10/1982 | Ayer | |
| 4,359,724 A | 11/1982 | Zimmerman et al. | |
| 4,595,013 A | 6/1986 | Jones et al. | |
| 4,638,807 A | 1/1987 | Ryder | |
| 4,685,466 A | * 8/1987 | Rau | ............ 600/387 |
| 4,969,468 A | 11/1990 | Byers et al. | |
| 5,305,746 A | 4/1994 | Fendrock | |
| 5,772,591 A | 6/1998 | Cram | |
| 6,032,064 A | 2/2000 | Devlin et al. | |
| 6,047,202 A | * 4/2000 | Finneran et al. | ............ 600/382 |
| 6,129,666 A | * 10/2000 | DeLuca et al. | ............ 600/393 |
| 6,301,493 B1 | * 10/2001 | Marro et al. | ............ 600/383 |
| 6,334,856 B1 | 1/2002 | Allen et al. | |
| 6,690,959 B2 | * 2/2004 | Thompson | ............ 600/393 |
| 2002/0019588 A1 | 2/2002 | Marro et al. | |

FOREIGN PATENT DOCUMENTS

| | | |
|---|---|---|
| WO | 01/52730 | 7/2001 |
| WO | 01/52731 | 7/2001 |
| WO | 02/32305 | 4/2002 |

OTHER PUBLICATIONS

*Micromachined Electrodes for Biopotential Measurements*, Patrick Griss et al., Journal of Microelectromechanical Systems, vol. 10, No. 1, Mar. 2001.

*Characterization of Micromachined Spiked Biopotential Electrodes*, Patrick Griss et al., IEEE Transactions on Biomedical Engineering, vol. 19, No. 6, Jun. 2002.

* cited by examiner

Primary Examiner—Lee S. Cohen
(74) Attorney, Agent, or Firm—Andrus, Sceales, Starke & Sawall, LLP

(57) ABSTRACT

A unitary, multi-electrode biopotential signal sensor is formed of injection molded plastic. A plurality of electrode areas containing spikes are defined in a base member of the sensor. The remaining areas of the base member are formed to have a greater flexibility than the electrode areas, as by being thinner or being perforated. The spikes and electrode areas of the base member are coated with a conductor layer to form the electrodes. Conductors on the base member lead to connectors to provide biopotential signals from the electrodes.

21 Claims, 3 Drawing Sheets

UNITARY MULTI-ELECTRODE BIOPOTENTIAL SIGNAL SENSOR AND METHOD FOR MAKING SAME

FIELD OF THE INVENTION

The present invention relates to medical electrodes that are applied to a patient's skin for obtaining electrophysiological biopotential signals such as EEG or ECG signals. Specifically, the present invention relates to a unitary, multi-electrode sensor for such purposes and to a method for making same.

BACKGROUND OF THE INVENTION

Electrodes applied to the skin of a patient are commonly employed to non-invasively obtain biopotential signals useful in determining a physiological condition or functioning of a patient. As the anatomy of mammalian skin presents a high electrical impedance and decreases the magnitude and the signal to noise ratio of the biopotential signal obtained by the electrode, it is common to abrade the skin and/or apply electrolytic gel to the skin before using the electrode to improve the electrical characteristics of the signal. See, for example, U.S. Pat. Nos. 5,305,746 and 6,032,064. These steps are time consuming, particularly when a number of electrodes are being applied to the patient. The '746 patent shows a disposable pre-gelled self-prepping electrode which is said to provide good electrical contact while reducing the work of removing the outer layer of skin and wetting the skin with electrolytic gel. The '064 patent shows a disposable pre-gelled, three electrode array. Both the electrode shown in the '746 patent and that shown in the '064 patent will have a finite shelf life as the electrolytic gel will dry out with time.

Another approach to improved electrode performance is to form needles on the electrode that penetrate the outer layer of the skin, thereby to reduce the electrode-skin impedance. See, for example, published PCT patent applications WO 01/52730 and WO 01/52731 and the articles Micromachined Electrodes for Biopotential Measurements, Griss et al., Journal of Microelectromechanical Systems, Vol. 10, No. 1, March 2001 and Characterization of Micromachined Spiked Biopotential Electrodes, Griss et al. in IEEE Transactions on Biomedical Engineering, Vol. 49, No. 6, June 2002. These references describe miniature needles micromachined on the surface of a silicon substrate and covered with a silver/silver chloride layer. The length of the spikes is typically 150 micrometers ($\mu$m) and the thickness is approximately 30 $\mu$m. See also U.S. Pat. No. 6,334,856 showing a device of similar configuration for use in drug delivery.

A particular, recent application for biopotential signal electrodes is to obtain electroencephalographic (EEG), biopotential signal data for objective quantification of the brain activity of a patient to determine the depth of anesthesia or level of consciousness of the patient. The need for such a determination has become increasingly desirable as the administration of anesthetic agents has become more sophisticated and from the efforts to administer anesthesia that is neither too deep nor too light. Anesthesia that is too light might result in the patient waking up during a surgical or other medical procedure while anesthesia that is too deep wastes expensive drugs and prolongs the recovery period for the patient.

Traditionally, electroencephalographic data has have been obtained by placing a plurality of electrodes on the scalp of the patient at locations specified in a recognized protocol. Applying the electrodes takes time and skill, may require skin preparation, and is especially difficult in areas of the scalp covered with thick hair.

However, in connection with EEG based depth of anesthesia measurements, it has recently been found that for many routine circumstances, it is sufficient to obtain electroencephalographic biopotential signals from only the forehead of the patient. The forehead is hairless and easy to access. This, to some extent, simplifies the application of the electrodes to the patient. However, to minimize the effects of external electrical interference, the electroencephalographic biopotential signals obtained from the patient's forehead or scalp are amplified using differential amplifiers. Such amplifiers have three inputs, a positive signal input, a negative signal input, and a ground input. Hence, the simplest one channel EEG signal measurement requires three electrodes for connection to the differential amplifier. Since it is usually desirable to obtain more than one channel of EEG signal data, numerous electrodes must still be applied to the patient to obtain the desired data so that the application time is not greatly shortened.

SUMMARY OF THE INVENTION

It is, therefore, the object of the present invention to provide an improved sensor that has multiple electrodes. The sensor can be easily and quickly applied to the skin of a patient to provide the number of electrodes required to obtain the desired biopotential signal data.

It is a further object of the present invention to provide a method for manufacturing such an electrode.

Briefly, the multi-electrode sensor of the present invention includes a base member formed of a non-conductive material, such as plastic. A plurality of electrode areas are defined in the base member. Each of the electrode areas has a plurality of spikes extending therefrom to penetrate the skin of the patient when the sensor is placed on the patient. The spikes, electrode areas, and base member comprise an integral, unitary structure of a common material. The portions of the base member not occupied by the electrode areas are rendered more flexible than the electrode areas to facilitate placement of the sensor on the skin of the patient. This may be accomplished by making those portions thinner or by perforating those portions. An electrically conductive coating, such as a silver/chloride layer is applied to the spikes and electrode area to form a plurality of biopotential signal electrodes on the base member. Electrical leads connected to the electrodes on the base member provide the biopotential signals from the electrode. An adhesive layer may be applied to a surface of the base member that abuts the skin of the patient to assist in securing the electrode to the patient when in use.

In the method for forming a unitary, multi-electrode biopotential sensor, a master of the sensor is formed for example, using a silicon element and a DRIE process. A mold is formed from this master and used to form the biopotential sensor having a base member and a plurality of spiked electrodes integrally formed at selected areas of the base member. The sensor may be formed by injection molding. The spiked electrode areas are then coated with an electrically conductive coating and electrical leads are connected to the electrodes for providing the biopotential signals from the sensor. An adhesive layer may be provided on portions of the base member not occupied by the electrodes.

The invention will be further appreciated by reference to the following detailed description taken in conjunction with the drawing.

DETAILED DESCRIPTION OF THE PREFERRED EMBODIMENTS

Figure 1:
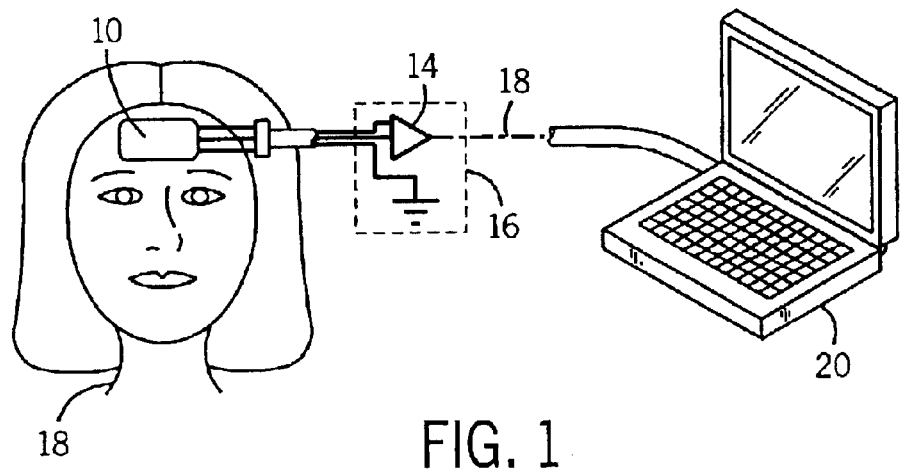
FIG. 1 is a general view of the unitary, multi-electrode biopotential signal sensor of the present invention in use with a patient.

FIG. 1 shows unitary, multi-electrode sensor 10 of the present invention applied to the forehead of a subject, such as patient 12. The sensor has three electrodes to provide a single channel of electroencephalographic (EEG) signal data, to differential amplifier 14 in signal processing circuit 16. The output of circuit 16 is connected via cable 18 to a computer 20 or other device for processing the signal data. For example, signal processing of the type described in published PCT patent application WO 02/32305, may be carried out to obtain an indication of the depth of anesthesia that patient 12 is experiencing. If an additional channel, or channels, of EEG signal data is/are required, additional sensors 10 may be applied to the forehead or scalp of patient 12. Or, a single sensor 10 may incorporate a further number of electrodes to provide the desired signal data.

Figure 2:
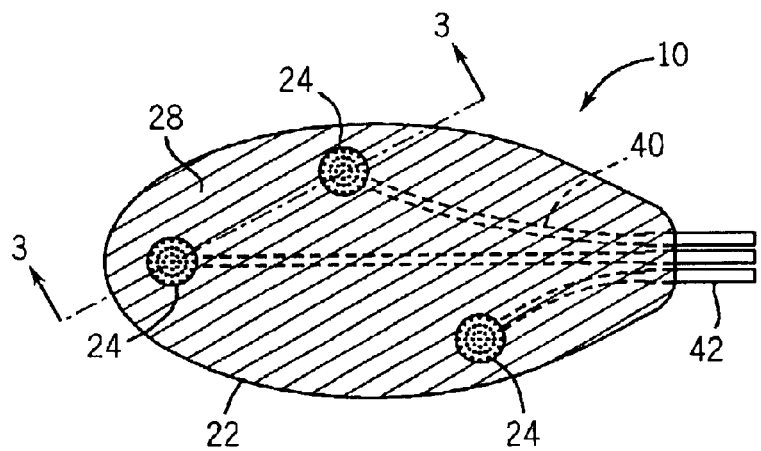
FIG. 2 is a plan view of the sensor of the present invention showing the side of the sensor applied to the skin of the patient.
Figure 3:
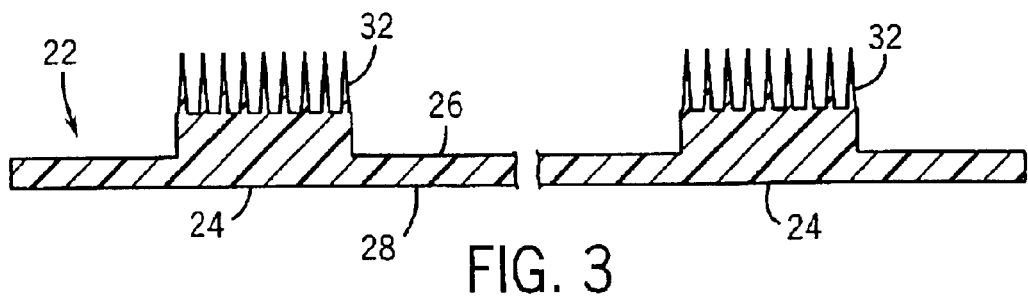
FIG. 3 is a cross sectional view of the sensor taken along the line 3—3 of FIG. 2.

Sensor 10 is formed as a unitary element of an injected molded plastic material, such as polycarbonate plastic. As shown in FIGS. 2 and 3, sensor 10 has base member 22 having a plurality of electrode areas 24 integrally formed therein on the surface 26 of base member 22 that will be adjacent the skin of patient 12 when electrode 10 is in use. In the embodiment shown in FIGS. 2 and 3, there are three electrode areas 24 to provide the three biopotential signals needed to form a single channel of EEG signal data.

Figure 4:
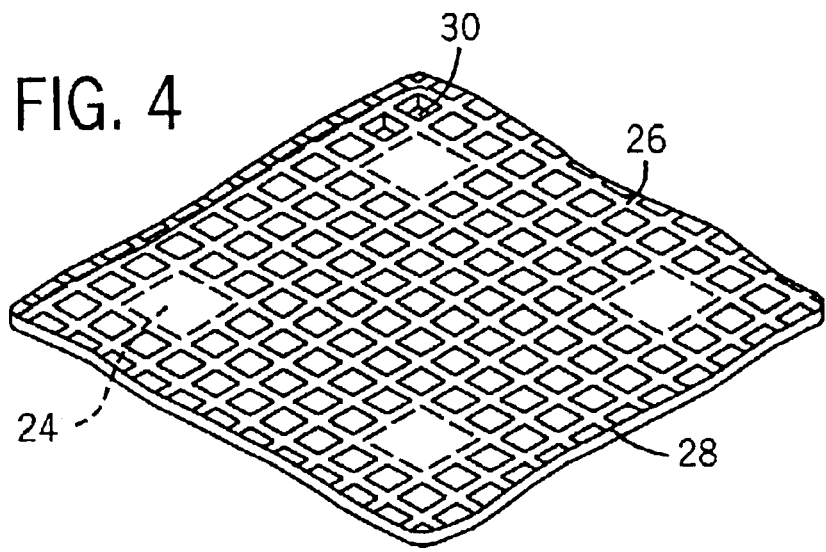
FIG. 4 is a fragmentary plan view showing an embodiment of the sensor of the present invention.

The portions 28 of base member 22 not occupied by electrode areas 24 are formed to possess a desired degree of flexibility so as to allow sensor 10 to form to the contours of the skin of patient 12 on which sensor 10 is placed. A variety of techniques may be used to render these portions 28 of base member 22 flexible. For example, portions 28 may be sufficiently thin in a direction normal to the surface 26 as to render it flexible. For material having the properties of polycarbonate plastic noted above, the thickness of portions 28 may be less than 0.5 mm, for example, 0.2 to 0.5 mm. Or, the portions 28 of base member 22 may be perforated with holes 30 as shown in FIG. 4 to provide the desired amount of flexibility to portion 28.

Figure 5:
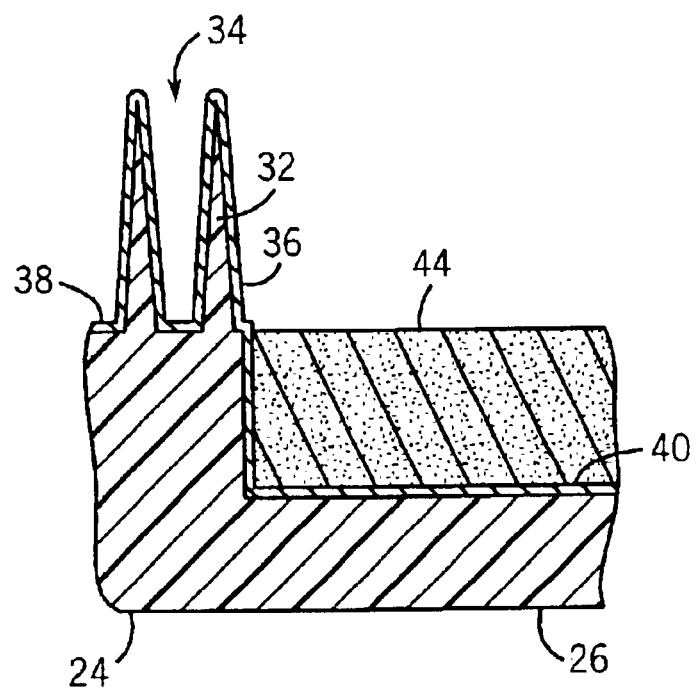
FIG. 5 is a fragmentary cross-sectional view similar to FIG. 3.

Spikes 32 are integrally formed with electrode areas 24, as shown in FIG. 3 and in detail in FIG. 5. Spikes 32 may be of any suitable shape. While somewhat pyramidal spikes are shown in FIGS. 3 and 5, the spikes may also be more columnar in nature with a sharpened point. The spikes need to be sufficiently sharp and rigid to penetrate the skin of patient 12 while being sufficiently elastic to prevent breaking off when exposed to lateral or bending forces. The spikes 32 are typically between 50 and 250 μm in length, preferably 150–180 μm in length. The length of the spikes in an electrode area may be varied if desired. The area of an electrode area 24 may be about 15–20 square millimeters and contain 300–500 spikes 32.

Electrode areas 24 formed in base member 22 desirably have sufficient stiffness to support and stabilize spikes 32 as they penetrate the skin of patient 12 when sensor 10 is applied to the patient. For this purpose, electrode areas 24 may be thicker than the portions 28 of base member 22 not comprising electrode areas 24, as shown in FIG. 3. In the exemplary embodiment described herein, the thickness of electrode areas 24 can be at least 0.5 mm and in preferably 0.5–1 mm, thick.

To form spikes 32 and the associated electrode area 24 into an electrode 34, the spikes are coated with a conductive layer 36, such as a silver—silver chloride layer. The surface 38 of electrode area 24 that is adjacent to the skin of patient 12 may also be, and preferably is, coated with such a layer. The coating 36 may also provide conductors 40 on base member 22 extending from the electrodes 34 to an edge of base member 22. Conductors 40 can be formed on the same side of base member as electrodes 34 or on the opposite side and connected to electrodes 34 by through-hole plating or some other suitable means. Suitable connectors 42, typically male connectors, can be coupled to an end of each conductor 40 to provide the biopotential output signals to signal processing equipment, such as differential amplifier 14 shown in FIG. 1. Electrodes 34 may be positioned on base member 22 at locations designated by protocol, at locations that provide the best quality signals, or at locations established by other considerations, such as the age or size of the patient.

The surface 26 of sensor 10 that will be adjacent to the skin of patient 12 may be provided with a coating of adhesive 44 to assist in retaining sensor 10 on the skin of patient 12. Preferably adhesive layer 44 is provided in the portions 26 of base member 22 not occupied by electrodes 34, as shown in FIG. 5.

It is not ordinarily necessary to use a wetting agent or conductive gel in conjunction with sensor 10 inasmuch as the penetration of the patient's skin by spikes 34 facilitates obtaining biopotential signals having the described properties. This feature plus the ability to apply a plurality of electrodes at the same time reduces the time needed to apply electrodes to the skin of patient 12 in the manner required to obtain the desired biopotential signal data.

While sensor 10 has been shown and described as obtaining EEG biopotential signals from the forehead of a patient, it will be appreciated that the sensor of the present invention may be used in other manners, for example as applied to the chest of a patient to obtain electrocardiographic (ECG) biopotential signal data or to a muscle of patient 12 to obtain electromyographic (EMG) biopotential signals.

While it is possible to form a unitary multi-electrode sensor of the present invention from silicon in the manner described in published PCT application WO 02/323051, silicon is a rather brittle material. To ensure that the spikes do not fracture when penetrating the skin of patient 12, it is necessary to carefully optimize the dimensions and profile of the spikes. Also, the cost of micromachining the spikes in a silicon wafer can be higher than desired.

A preferred method of making the present invention is thus to replicate the sensor structure in plastics, using a mold obtained from a micromachined silicon master.

Figure 6:
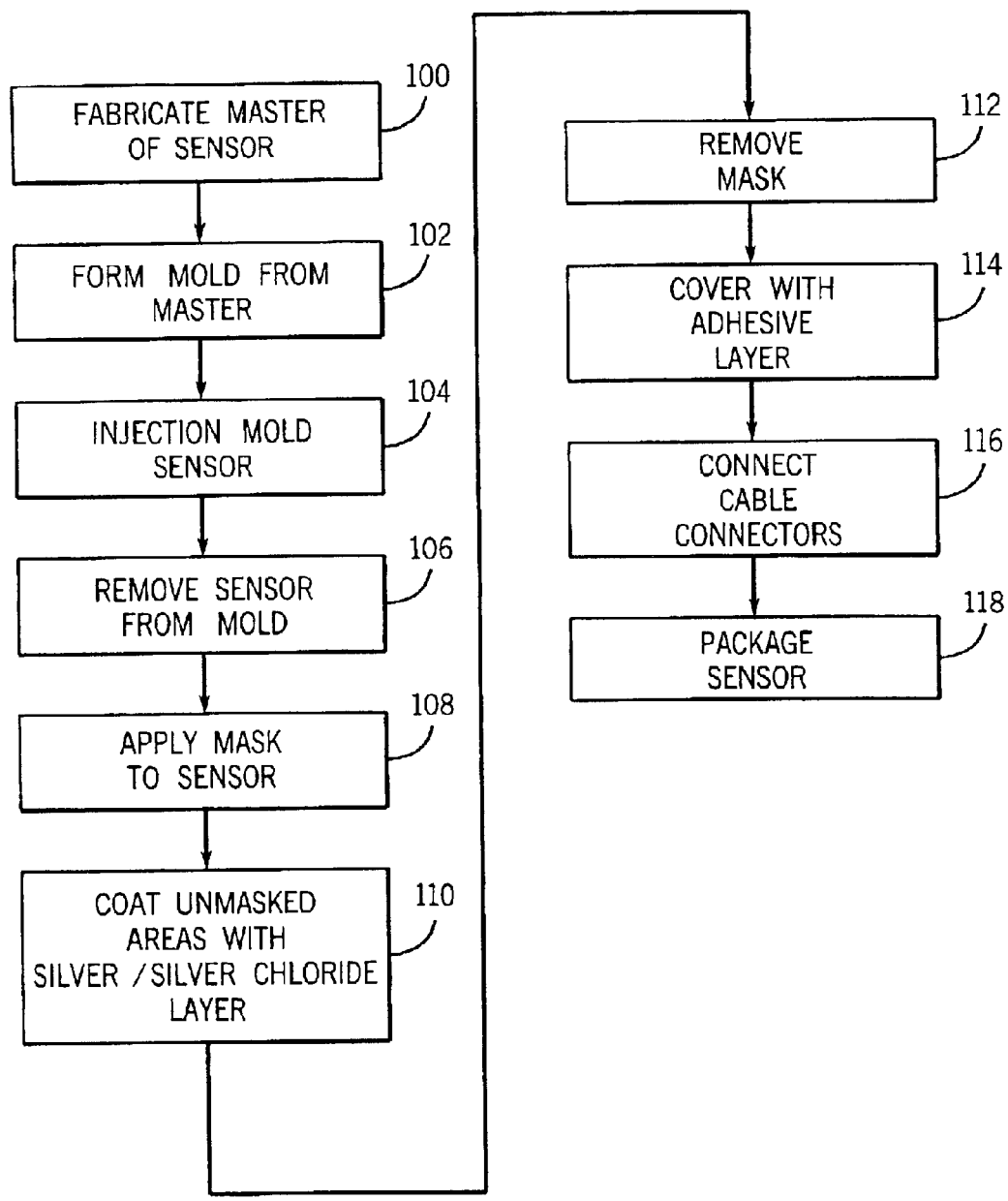
FIG. 6 is a flow chart illustrating a method for manufacturing the sensor.

As shown in FIG. 6, to carry out the process of the present invention for forming sensor 10, a master of the unitary, multi-electrode sensor is fabricated in silicon using a micromachining technique such as a deep reactive ion etching (DRIE) process. See step 100. The master is then used to form a mold, in step 102. Importantly, the master or mold is configured to form the portions 28 of base member 22 of sensor 10 to be sufficiently thin or perforated as to provide the necessary flexibility to these portions of the sensor.

Sensor 10 is then formed, in step 104, by injection molding a plastic material, such as polycarbonate plastic material, under vacuum conditions into the mold formed in step 102. Thereafter, in step 106, the sensor structure is removed from the mold.

An appropriate mask defining the electrode areas 24 and spikes 32 of electrodes 34 is placed on surface 26 that will be contiguous with the skin of patient 12 when the sensor is applied. See step 108. The mask may also be used to define conductors 40 of sensor 10. Silver—silver chloride layer 30 is then coated on the unmasked areas, as by electrodeposition. Thereafter, the mask is removed from surface 26 of base member 22 at step 112. The surface 26 of base member 18 is then covered with adhesive layer 44, preferably in the portions 28 of base member 22 not forming electrodes 34. See step 114. Cable connectors 34 electrically connected to conductors 32 are then mounted on base member 18, at step 116.

The completely formed sensor 10 may then be placed in suitable packaging to protect electrodes 28 as well as adhesive layer 36 at step 118.

It is recognized that other equivalents, alternatives, and modifications aside from those expressly stated, are possible and within the scope of the appended claims.

What is claimed is:

1. A unitary, multi-electrode sensor for detecting biopotential signals from the skin of a subject, said sensor comprising:
   a base member formed of a non-conductive material and having a surface suitable for being placed in contiguity with the skin of the subject;
   a plurality of electrode areas defined in said surface of said base member, each of said electrode areas having a plurality of spikes extending therefrom for penetrating the skin of the subject when the sensor is placed on the skin of the subject, said spikes and the electrode areas defined in said base member comprising an integral structure of a common material, said common material possessing structural properties and being formed such that said spikes have sufficient stiffness to penetrate the subject's skin, the electrode areas have sufficient stiffness to support and stabilize said spikes, and the portions of said base member not occupied by said electrode areas are more flexible than said electrode areas to facilitate placement of the sensor on the skin of the subject;
   an electrically conductive coating applied at least to said spikes of each of said electrode areas to form a biopotential signal electrode from each of said electrode areas on said surface of said base member; and
   an electrical lead electrically coupled to the spikes of each of said electrodes for providing biopotential signals from said electrodes.

2. The multi-electrode sensor of claim 1 wherein said electrically conductive coating is applied to said electrode areas to form said biopotential signal electrodes.

3. The multi-electrode sensor of claim 1 wherein said electrode areas are thicker in a dimension generally normal to said surface than portions of said base member not occupied by said electrode areas.

4. The multi-electrode sensor of claim 3 wherein the thickness of said electrode areas is at least approximately 0.5 mm and the thickness of portions of said base member not occupied by said electrode areas is less than approximately 0.5 mm.

5. The multi-electrode sensor of claim 4 wherein said thickness of said electrode areas is between 0.5 and 1 mm and the thickness of portions of said base member not occupied by said electrode areas is between 0.2 and 0.5 mm.

6. The multi-electrode sensor of claim 1 wherein portions of said base member not occupied by said electrode areas contain perforations for rendering said portions of said base member flexible.

7. The multi-electrode sensor of claim 1 wherein said sensor is formed to detect a biopotential signal from the skin of the subject by said electrodes in the absence of a wetting agent or conductive gel.

8. The multi-electrode sensor of claim 1 wherein said electrical leads are formed from an electrically conductive layer on said base member.

9. The multi-electrode sensor of claim 8 wherein said electrical leads are formed from said electrically conductive coating.

10. The multi-electrode sensor of claim 1 including connectors on said base member, said electrical leads being connected to said connectors.

11. The multi-electrode sensor of claim 10 wherein said connectors are located on an edge of said base member.

12. The multi-electrode sensor of claim 10 wherein said connectors are formed as male connector members.

13. The multi-electrode sensor of claim 1 further including an adhesive layer on said surface of said base member.

14. The multi-electrode sensor of claim 13 wherein said adhesive layer occupies portions of said surface not occupied by said electrode areas.

15. The multi-electrode sensor according to claim 1 wherein said common material of said sensor is a plastic material.

16. The multi-electrode sensor according to claim 15 wherein said common material of said sensor is a polycarbonate material.

17. The multi-electrode sensor according to claim 15 wherein said sensor is formed of injection molded plastic material.

18. The multi-electrode sensor according to claim 1 further defined as one for obtaining EEG biopotential signals from the head of the subject.

19. The multi-electrode sensor according to claim 18 further defined as one for obtaining EEG biopotential signals from the forehead of a subject.

20. The multi-electrode sensor of claim 1 further defined as one for obtaining electrocardiographic signals from the body of the subject.

21. The multi-electrode sensor of claim 1 further defined as one for obtaining electromyographic signals from the body of the subject.

* * * * *